United States Patent [19]

Earles

[11] Patent Number: 5,766,579
[45] Date of Patent: Jun. 16, 1998

[54] COMPOSITION AND METHOD FOR TREATMENT OF DERMATITIS ON THE SCALP

[76] Inventor: R. Martin Earles, 1328 Plymouth Ct., Chicago, Ill. 60605

[21] Appl. No.: 778,964

[22] Filed: Jan. 6, 1997

Related U.S. Application Data

[62] Division of Ser. No. 401,346, Mar. 9, 1995, Pat. No. 5,362,975.

[51] Int. Cl.⁶ ........................................ A61K 7/06
[52] U.S. Cl. ............... 424/70.1; 424/401; 424/70.11; 424/70.5; 514/864; 514/880; 514/944
[58] Field of Search ................. 424/401, 70.1, 424/70.5, 70.11; 514/864, 880, 944

[56] References Cited

U.S. PATENT DOCUMENTS

| | | | |
|---|---|---|---|
| 2,160,030 | 5/1939 | Nitsche | 252/6 |
| 2,884,352 | 4/1959 | Brenner et al. | 167/20 |
| 3,476,489 | 11/1969 | Mees et al. | 424/164 |
| 4,002,734 | 1/1977 | Pickford | 424/74 |
| 4,237,112 | 12/1980 | Selega et al. | 424/70 |
| 4,333,927 | 6/1982 | Ofuchi et al. | 424/58 |
| 4,722,837 | 2/1988 | Cameron | 424/70 |
| 4,835,148 | 5/1989 | Barford et al. | 514/179 |
| 4,846,844 | 7/1989 | DeLeon et al. | 623/66 |
| 4,849,214 | 7/1989 | Ruiseco | 424/74 |
| 4,853,379 | 8/1989 | Shroot et al. | 514/179 |
| 4,902,682 | 2/1990 | Sattler et al. | 514/179 |
| 4,913,852 | 4/1990 | Milioni et al. | 514/179 |
| 4,918,065 | 4/1990 | Stindl et al. | 514/179 |
| 4,959,205 | 9/1990 | Brunner et al. | 424/59 |
| 5,002,938 | 3/1991 | Wang et al. | 514/171 |
| 5,061,700 | 10/1991 | Dow et al. | 514/169 |
| 5,082,663 | 1/1992 | Konishi et al. | 424/445 |
| 5,112,816 | 5/1992 | Narui et al. | 514/179 |

OTHER PUBLICATIONS

Carr et al., "Treatment of Seborrhoeic Dermatitis with Ketoconazole: I. Response of Seborrhoeic Dermatitis of the Scalp to Topical Ketoconazole", *British J. of Derm.* 116 (1987) 213–216.

*Dermatology*, Moschella et al., eds., W.B. Saunders Co. (1992), pp. 96–98, 136–137.

*Dermatology in General Medicine*, McGraw Hill, pp. 75–76.

Farr et al., "Treatment of Seborrhoeic Dermatits with Topical Ketoconazole", *The Lancet*, (1984) 1271–1272.

Green et al., "Treatment of Seborrhoeic Dermatitis with Ketoconazole: II. Response of Seborrhoeic Dermatitis of the Face, Scalp and Trunk to Topical Ketoconazole", *British J. of Derm.* 116 (1987) 217–221.

Skinner et al., "Double-Blind Treatment of Seborrheic Dermatitis wth 2% Ketoconazole Cream", *J. of the American Acad. of Derm.*, 12 (1985) 852–856.

Stratigos et al., "Ketoconazole 2% Cream Versus Hydrocortisone 1% Cream in the Treatment of Seborrhoeic Dermatitis", *J. of the American Acad. of Derm.*, 19 (1988) 850–852.

*Textbook of Dermatology*, Champion et al., eds., Blackwell Scientific Pub., pp. 471, 551.

*Primary Examiner*—Jyothsan Venkat
*Attorney, Agent, or Firm*—Fitch, Even, Tabin & Flannery

[57] ABSTRACT

The invention provides a composition for treating seborrheic dermatitis on the scalp, a method for treating seborrheic dermatitis and a method for making the composition of the invention. The composition of the invention, which is not a shampoo and does not contain any soap or detergent for cleaning hair, is a unique scalp medicament blend of ingredients. The composition comprises from about 0.5 to about 2.5 weight percent, based upon the weight of the composition, hydrocortisone; from about 2.5 to about 7.5 weight percent elemental sulfur; and from about 90 to about 97 weight percent of an active vehicle comprising a generally neutral hydrocarbon jelly, such as petrolatum or petroleum jelly, and gelled aqueous carboxypolymethylene.

2 Claims, No Drawings

COMPOSITION AND METHOD FOR TREATMENT OF DERMATITIS ON THE SCALP

CROSS-REFERENCE TO RELATED APPLICATIONS

This application is a Divisional application of U.S. patent application Ser. No. 08/401,346, filed Mar. 9, 1995 and issued May 27, 1997, as U.S. Pat. No. 5,632,975.

This invention is directed to a medicament composition which is a blend of ingredients for the treatment of seborrheic dermatitis on the scalp, a method for the treatment of seborrheic dermatitis and a method for making the medicament blend without the application of heat while blending the ingredients.

BACKGROUND OF THE INVENTION

The anti-inflammatory effects of hydrocortisone and its affects on the skin are known. Indeed, U.S. Pat. No. 4,722,837 to Cameron and U.S. Pat. No. 4,835,148 to Barford et al. describe cortisone being applied to the scalp as shampoos for the therapeutic effect of the cortisone. These compositions, however, contemplate a shampoo base and application with copious amounts of water.

Elemental sulfur also is known to have a beneficial effect in the treatment of skin diseases. The '837 patent to Cameroon describes the application of sulfur with cortisone as a shampoo. That composition as indicated requires application with copious amounts of water because it is a shampoo. Application of water in connection with shampooing may remove skin oils which may exacerbate dry flaky skin. The dry flaking skin contributes to a part of the dermalogical problem which is the subject of the shampoo treatment. U.S. Pat. No. 3,476,489 to Mees et al. also describes a shampoo with sulfur, but without cortisone, and is subject to the same drawbacks as Cameroon. U.S. Pat. No. 4,002,734 to Pickford describes a blend of ingredients for the treatment of the scalp which is not a shampoo, and which includes sulfur. That blend, however, also includes ingredients such as lanolin, coal tar and phenol which can exacerbate dermatitis.

Indeed, most products for the treatment and relief of seborrheic dermatitis are shampoos despite the fact daily or frequent washing of the hair often will dry the scalp. Further, it has been thought that ointments should not be applied to the scalp. Hence, the therapeutic effects of hydrocarbon jellies on the scalp largely have been ignored. Moreover, the preference of many individuals not to frequently shampoo such as for the sake of cosmetic appearance also have been ignored.

The need to frequently use shampoos for relief of seborrheic dermatitis is especially a problem for persons with hair with tight curls or waves, such as African-Americans. Frequent shampooing not only results in drying of the scalp, but also interferes with the cosmetic effect of hair beautification treatments often used in the African-American community.

Frequent shampooing is not typically done after receiving the cosmetic hair straightening process known as "the press and curl." During this process, which can take up to one hour, not including shampooing, drying and styling, the hair is straightened with a heated comb and curled with a curling iron. The resulting curl derived from this process is immediately lost when the hair comes in contact with water, and is not restored by simply blow drying. The hair also reverts to its state of tight curls and waves, known as "going back". Persons who employ this style usually have their hair washed only by their beauticians at two week or more intervals.

Individuals who have the permanent wave type hairstyle also find frequent shampooing undesirable. Individuals wearing a permanent wave hairstyle may wash their hair at weekly or bimonthly intervals, followed by the use of curlers or curling iron. Contact with water results in the loss of the curl or wave, but the hair does not revert to the state having tight curls or waves. The lack of regular or frequent washing in individuals wearing a press and curl or permanent wave, and the absence of an effective and cosmetically acceptable treatment, predisposes these individuals to increased incidence of seborrheic dermatitis.

With the advent of newer hair styles in which adhesive gels are applied to the hair, the hair is left undisturbed for a week at a time without combing, brushing and shampooing. Hence, this hairstyle does not lend itself to methods of preventing or treating seborrheic dermatitis with shampooing, and instead contributes to conditions which favor the advancement of seborrheic dermatitis. This problem is often more severe for individuals with braided hairstyles. With the braided hairstyle, the hair is braided and often artificial hair is weaved, glued or otherwise bonded to the hair to make it longer. The hair may remain in this condition for two to three months. The hair may be washed at two to four-week intervals, however, the braided hair prevents thorough washing away of scale and debris which contributes to conditions which favor the advancement of seborrheic dermatitis and bacterial infections.

OBJECTS OF THE INVENTION

An object of the invention is to provide a medicament composition for the treatment of dry flaky scalp often caused by seborrheic dermatitis on the scalp which composition is not a shampoo and which does not require the cleaning of the hair or application of water with the application of the composition to the surface of the scalp.

Another object of the invention is to provide a method of treating seborrheic dermatitis on the scalp by providing a medicament composition which may be applied without having a deleterious effect upon hair styles and mitigates any greasy appearance of the hair upon application of the medicament composition.

Yet another object of the invention is to provide a method of making the composition of the invention by dispersing the sulfur in the composition without the application of heat during the dispersal of the sulfur.

These and further objects and advantages of the invention will be found by reference to the following description.

SUMMARY OF THE INVENTION

The invention provides a composition for treating seborrheic dermatitis on the scalp, a method for treating seborrheic dermatitis and a method for making the composition of the invention. The composition of the invention, which is not a shampoo and does not contain any soap or detergent for cleaning hair, is a unique scalp medicament blend of ingredients which comprises hydrocortisone, particulate sulfur, hydrocarbon jelly and carboxypolymethylene (a gel forming agent). Quantitatively, the composition comprises from about 0.5 to about 2.5 weight percent, based upon the weight of the four-component composition, hydrocortisone; from about 2.5 to about 7.5 weight percent elemental sulfur; from about 90 to about 97 weight percent of the active vehicle which comprises a generally neutral hydrocarbon jelly, such as petrolatum or petroleum jelly and gelled carboxypolymethylene. The carboxypolymethylene is gelled with water and provides water to the scalp and which is in an amount in the blend effective for reducing the greasy appearance in the hair which would be caused by the hydrocarbon jelly. Generally, the four-component composition comprises from about 5 to about 90 weight percent carboxypolymethylene gel and from 90 to about 10 weight percent hydrocarbon jelly. The percentages are based upon the weight of the four-part composition. The topical application of the composition of the invention to the surface of the scalp provides a layer that not only retains moisture in the scalp, but with the use of the carboxypolymethylene provides moisture to the scalp in addition to the moisture already in the skin which is retained therein by the composition. Generally, prior to jelling with water, the blend comprises from about 0.2 to about 0.4 weight percent, based upon the weight of the composition, carboxypolymethylene. In another important aspect, the composition includes from about 3 to about 5 weight percent glycerin to provide softness and sheen to the hair. In yet another important aspect of the invention, the composition includes propylene glycol in an amount effective to disperse particulate sulfur having a particle size of not more than one micron in the glycol for later dispersal and suspension of the particulate sulfur in the hydrocarbon jelly.

The method of the invention for treating seborrheic dermatitis comprises contacting the scalp medicament blend with the scalp, generally without the simultaneous application of water from a source additional to the composition, soap or detergents for cleaning hair. The composition of the invention is topically applied and preferably gently rubbed into the surface of the scalp.

The method of making the composition includes blending sulfur and propylene glycol without the addition of heat to disperse the sulfur in the propylene glycol and for later dispersal of the latter blend into the hydrocarbon jelly and carboxypolymethylene to provide the composition of the invention. In an important aspect of the invention, one part sulfur is combined with propylene glycol, where the ratio of particulate sulfur to propylene glycol is in the range of from about 1:1 to about 1:1.5 sulfur to propylene glycol, until the sulfur is dispersed and a fine cream is obtained. Thereafter the hydrocortisone is blended into the latter blend to provide a hydrocortisone blend with the hydrocarbon jelly and the carboxypolymetilylene thereafter being blended into the hydrocortisone blend.

DESCRIPTION OF THE PREFERRED EMBODIMENTS OF THE INVENTION

Definitions

"Hydrocortisone" includes hydrocortisone, methylprednisolone, dexamethasone, triamcinolone, triamcinolone acetonide, flumethasone, fluocinonide, beclomethasone, betamethsone, fluocinolone, fluorometholone, fludroxycortide, clobetasone, clobetasol and esters ketals, acetals, hemiacetals, ethers and alkylates such as acetates.

"Hydrocarbon jelly" means a mixture of generally non-straight chain solid hydrocarbons which may include liquid hydrocarbons. These hydrocarbons are primarily of the methane series having the general formula $C_nH_{2n+2}$ and often are called petroleum jelly, petrolatum, white petrolatum, paraffin jelly, vaseline and cosmoline. Any equivalent petroleum gel will function in the invention if it is dermatologically acceptable. The hydrocarbon jelly is a composition which retains moisture in the skin and aids penetration of the hydrocortisone and sulfur into the scalp.

"Shampoo" means a composition for cleaning hair, the composition usually including a soap and/or a detergent and is used with a source of water additional to or outside of the shampoo composition.

"Sulfur" means elemental sulfur which is finely divided such as flowers of sulfur. According to the invention, the sulfur has a particle size of not more than about one micron and preferably from about 0.75 to about one.

"Carboxypolymethylene" means a carboxyvinyl polymer with active carboxyl groups. These polymers are sold commercially as Carbomer and Carbopol polymers.

"Scalp medicament" and "scalp medicament blend" mean a composition which is not a shampoo which is used in therapy for the treatment of the scalp.

The terms "treating" and "treatment" as used herein refer to eliminating or reducing the symptoms of a disease or disorder, preventing the symptoms or disorder from increasing in severity, and preventing the disorder form occurring in the first instance.

Symptoms of seborrheic dermatitis of the scalp include inflammation, itching and flaking of skin from the head.

The Scalp Medicament Blend

The composition of the invention is a blend of hydrocortisone, sulfur, hydrocarbon jelly and gelled carboxypolymethylene which blend is a scalp medicament for topical application to the scalp. The medicament blend is topically applied to the surface of the scalp in an amount and at a frequency effective for the control of itching, flaking and scaling of the scalp and remains on the scalp not only to control the symptoms of dryness and itch, but also to treat and obviate the source of such symptoms, such as a yeast infection, without requiring frequent shampooing. The medicament blend is easily applied to the scalp and if a fragrance is included in the blend in an amount effective for masking the odor of the sulfur, the objectionable nature of a sulfur containing medicament composition is overcome. Further, it has been surprisingly found that even though the blend contains a hydrocarbon jelly, the blend aids in grooming and manageability of the hair and provides it with a cosmetically desirable body and sheen, while not disrupting the existing hairstyle.

Generally, hydrocortisone compounds with anti-inflammatory effects are suitable components of the blend. Examples of hydrocortisone compounds includes those mentioned previously. The blend contains from about 0.5 to about 2.5 weight percent, based on the weight of the four-component blend, of hydrocortisone. Preferably, the blend contains from about 0.75 to about 1.5 weight percent hydrocortisone.

The four-component medicament blend contains from about 2.5 to about 7.5 weight percent, based on the weight of the blend, of sulfur, preferably, from about 4.5 to about 5.5 weight percent sulfur. Sulfur is beneficial in controlling yeast such as *Pityrosporum ovate*, which is associated with seborrheic dermatitis.

Seborrheic dermatitis causes flaking and scaling of the scalp which disrupts the epidermal integrity of the scalp. Shampoos effective for treating seborrheic dermatitis do nothing to relieve dryness or flaking and may even aggravate these symptoms. The blend of the present invention addresses these problems by not being a shampoo which removes oils and moisture from the skin but retains body oil and moisture by including a hydrocarbon jelly. Although not a shampoo, the blend comprises from about 90 to 97 weight percent of a therapeutically active vehicle for delivery of the particulate sulfur and hydrocortisone to the scalp. The therapeutically active vehicle comprises of hydrocarbon jelly and gelled carboxypolymethylene. Acceptable hydrocarbon jelly compositions include neutral hydrocarbon jelly, such as petrolatum or petroleum jelly. Upon topical application of the medicament blend, the hydrocarbon jelly provides a layer to prevent skin moisture and oil loss, acts to reestablish the epidermal barrier in the scalp and aids in rehydration of the skin, to decrease itching.

In addition to its own therapeutic activity, the hydrocarbon jelly also acts to keep the other components of the blend in contact with the skin to provide a continuous therapeutic benefit. Shampoos and oily liquids are not effective to provide a constant adherence to the scalp that is provided by this invention.

The therapeutically active vehicle further contains carboxypolymethylene in an amount in the blend effective for reducing the greasy appearance in the hair caused by the hydrocarbon jelly. Carboxypolymethylene is gelled with an amount of water effective for providing a gel, such as from about 71 to about 86 weight percent water, based on the weight of the carboxypolymethylene. The jelled carboxypolymethylene, when incorporated into the medicament blend, provides water to the scalp and hair and acts to reduce the greasy appearance of the hair caused by the hydrocarbon jelly. The water hydrates the scalp to reduce itching and hydrates the hair to reduce breakage of the hair. In an important aspect, the medicament blend contains from about 0.2 to about 0.4 weight percent, based on the weight of the blend, of ungelled carboxypolymethylene.

In another important aspect of the invention, it has been found that glycerin when added to the gel and the composition provides hair with softness, sheen and a slightly oily feel that is considered pleasing to look at and to feel by its users. The slipperiness of the hair, as contributed to by the glycerin also decreases breakage attendant with routine hair care. In this aspect the composition comprises from about 3 to about 5 weight percent of the composition.

In an important aspect of the invention, the blend contains a fragrance or mixture of fragrances. The fragrance provides the blend with a pleasing smell which makes the use of the blend more attractive and helps to overcome the objectionableness normally associated with sulfur containing compounds. Fragrances which are effective for addition to the blend include Oil of Bergamot and lemon oil. When fragrance is present in the blend, the blend contains an effective amount of fragrance to mask the odor of the sulfur which is generally from about 0.5 to about 5.0 weight percent, based on the weight of the blend, of fragrance.

Optionally, the blend may also contain antibiotics or mixtures of antibiotics. Bacterial infections frequently result from the scratching that is attendant with seborrheic dermatitis. The addition of antibiotics to the blend provides significant antibacterial activity above that obtained by the sulfur alone. Antibiotics in the blend of the invention are useful in treating individuals with bacterial infections and in preventing infections in individuals predisposed to infections. Typical antibiotics which may be used in this invention include aminoglycosides, such as gentamicin, kanamycin, neomycin, paromomycin, streptomycin, or tobramycin; ansamycins, such as rifamycin, or rifampin; cephalosporins, such a cephalexin, cephaloridine, cephalothin, cefazolin, cephapirin, cephradine, or cephaloglycin; chloramphenicols; macrolides, such as erythromycin, tylosin, oleandomycin, or spiramycin; penicillins, such as penicillin G & V, phenethicillin, methicillin, oxacillin, cloxacillin, diclosxacillin, floxacillin, nafcillin, ampicillin, amoxicillin, or carbenicillin; sulfonamide; tetracyclines, such as tetracycline, oxytetracycline, chlortetracycline, methacycline, demeclocycline, rolitetracycline, doxycycline, or iminocylcline; trimethoprim-sulfamethoxazole; polypeptides, such as bacitracin, polymyxins, tyrothricin, or vancomycin; and miscellaneous antibiotics, such as lincomycin, clindamycin, or spectinomycin.

One aspect of the invention which includes antibiotics, the blend includes from about 0.25 to about 0.045 weight percent neomycin, from about 4000 to about 6000 units of polymyxin, from about 300 to about 500 units of bacitracin and an a therapeutically effective amount of bactroban.

In one aspect of the invention, the medicament blend is in the form of a gel. In this aspect, the blend comprises up to about 90 weight percent, based upon the weight of the four-component composition, of a gel made from a gelling agent such as Carbomer 940 or Carbomer 942 and the hydrocarbon jelly comprises from about 7 weight percent of the medicament blend. The amount of gel used may be a function of the type of hair to which the medicament blend is applied. For thin, fine hair, the gel composition provides thicker-looking, manageable hair. For tightly curled hair, the medicament blend may comprise only from about 5 to about 10 weight percent carboxymethylene gel and about 85 to about 80 weight percent hydrocarbon jelly.

In another aspect of the invention, the blend of the invention may be a cream by decreasing the amount of active vehicle and adding a cream which may be suitably applied to the hair. In this aspect of the invention the medicament blend comprises suitable hair creams which include vitapointe and/or cold cream in an amount effective for providing a creamy texture to the composition. The creamy composition may suitably include from about 35 to about 60 percent by weight, hair cream, from about 15 to about 40 weight percent hydrocarbon jelly and from about 10 to about 20 weight percent of a gel from a gelling agent as described above.

The following composition is representative of the invention.

| Component | Weight % Based on Weight of the Composition |
| --- | --- |
| Hydrocortisone | 0.5 to 2.5 |
| Sulfur | 2.5 to 7.5 |
| Petrolatum | 14.0 to 87.0 |
| Carboxypolymethylene | 0.2 to 0.4 |
| Glycerin | 3.0 to 5.0 |
| Oil of Bergamot | 0.5 to 5.0 |
| Polymyxin B Sulfate | 4000 to 6000 units |
| Neomycin | 0.025 to 0.035 |
| Bacitracin Zinc | 300 to 500 units |
| Cold Cream | 0 to 60.0 |

Method for Treating Seborrheic Dermatitis

The method for treating seborrheic dermatitis according to the invention requires topical application of the medicament blend to the scalp on an average of about once a day. The blend may be applied to the scalp by parting the hair and gently rubbing in a small amount into the scalp and allowing it to remain until the next shampoo of the hair, which may be days or weeks. Further, the blend may be applied by placing a small amount into the palms of the hands and spreading it over the hands into the hair. The hair is rubbed until all traces of the material have disappeared.

Method of Making a Scalp Medicament Blend

The composition of the invention may be made by blending the ingredients with the application of heat to obtain the composition of the invention and dispersion of the particulate sulphur generally uniformly throughout the blend. One aspect of this invention, however, is that a method for making the composition of the invention is provided where the method of making the composition does not require the application of external heat to disperse the sulfur in the hydrocarbon jelly and carboxypolymethylene gel. In accordance with this aspect of the invention, particulate sulfur having a particle size of not more than about one micron, is blended with propylene glycol. Generally, from about one part of particulate sulfur is blended with from about 1.0 to about 1.5 parts propylene glycol to provide a sulfur dispersion. In an important aspect of the invention, about one part particulate sulfur is blended with one and one/half part propylene glycol. Blending can be conducted without heating for an amount of time effective to disperse the particulate sulfur into the propylene glycol to provide the sulfur dispersion. The dispersion of particulate sulfur in the polypropylene glycol provides a preparation with fine particles of sulfur which maximizes effectiveness. The sulfur dispersion is further blended with hydrocortisone, a hydrocarbon jelly, and carboxypolymethylene.

A fragrance may also be added to the mixture and further blended. Fragrances which are effective for addition to the blend include oil of bergamot and lemon oil. As mentioned previously, antibiotics may also be added to the blend.

Varying degrees of hydrocarbon jelly, gel and haircream can be admixed to adjust for varying degrees of dryness of the scalp and the desired cosmetic effect on the hair. In the aspect of the invention which includes propylene glycol, the medicament blend comprises from about 0.03 to about 0.04 weight percent propylene glycol.

The following examples illustrate methods for carrying out the invention and should be understood to be illustrative of, but not limiting upon, the scope of the invention which is defined in the appended claims.

EXAMPLE I

Particulate sulfur (454 grams) is blended with 275 ml of propylene glycol at ambient temperature until the sulfur is fully dispersed.

Hydrocortisone (454 grams) is added to the sulfur dispersion and the mixture is blended for 15 minutes. Oil of Bergamot (10 ml) is added to the latter blend and blended for 3 minutes. Carbomer (26 grams) is gelled with 1130 ml of water. The gelled Carbomer is blended with the hydrocortisone/sulfur/propylene glycol blend for 10 minutes. Glycerin (200 cc) is blended with the hydrocortisone/sulfur/propylene glycol blend. The final product has a slightly yellow color with slightly oily consistency.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A method for treating seborrheic dermatitis comprising applying a scalp medicament blend to the surface of the scalp in an amount and at a frequency effective for control of itching, flaking and scaling of the scalp, the blend consisting essentially of:

from about 0.5 to about 2.5 weight percent, based upon the weight of the blend, hydrocortisone;

from about 2.5 to about 7.5 weight percent, based upon the weight of the blend, sulfur;

from about 2 to about 5 weight percent, based upon the weight of the blend, glycerin;

propylene glycol in a ratio in the range of from about one part sulfur to about 1.0 part to about 1.5 parts propylene glycol;

an active vehicle comprising from about 90 to about 97 weight percent based upon the weight of the blend, hydrocarbon jelly and carboxypolymethylene, the carboxypolymethylene comprising from about 0.2 to about 0.4, weight percent, based upon the weight of the blend; and water in an amount effective for gelling the carboxypolymethylene.

2. A method for treating seborrheic dermatitis as recited in claim 1, wherein the hydrocortisone comprises from about 0.5 to about 1.5 weight percent of the blend and the sulfur comprises from about 4.5 to about 5.5 weight percent of the blend.

* * * * *